United States Patent [19]

Coleman et al.

[11] Patent Number: 4,736,063

[45] Date of Patent: Apr. 5, 1988

[54] SORBIC ACID PROCESS

[75] Inventors: James P. Coleman; Richard C. Hallcher, both of Maryland Heights; Dudley E. McMackins, St. Charles, all of Mo.

[73] Assignee: Monsanto Company, St. Louis, Mo.

[21] Appl. No.: 222,201

[22] Filed: Jan. 2, 1981

[51] Int. Cl.$^4$ .................... C07C 51/377; C07C 57/10
[52] U.S. Cl. .................... 562/599; 560/241; 560/262; 562/601
[58] Field of Search ............ 562/599, 601; 560/241

[56] References Cited

U.S. PATENT DOCUMENTS

| | | | |
|---|---|---|---|
| 3,927,051 | 12/1975 | de Kline | 260/413 |
| 3,992,417 | 11/1976 | Dessau et al. | 260/343.6 |
| 4,011,239 | 3/1977 | Heiba et al. | 260/327 S |
| 4,014,910 | 3/1977 | de Kline | 260/413 |
| 4,022,822 | 5/1977 | Isujino et al. | 562/601 |
| 4,158,741 | 6/1979 | Goi et al. | 562/601 |
| 4,175,089 | 11/1979 | Heiba et al. | 260/343.6 |

FOREIGN PATENT DOCUMENTS

| | | | |
|---|---|---|---|
| 3819106 | 5/1966 | Japan | 562/601 |
| 48-15186 | 2/1973 | Japan | 562/598 |
| 1128375 | 9/1968 | United Kingdom | 562/598 |
| 1219332 | 1/1971 | United Kingdom | |

OTHER PUBLICATIONS de Klein, W. J., Recl. Trav. Chim., vol. 94, pp. 48–50.
de Klein, W. J., J. Royal Netherlands Chemical Society, vol. 94, pp. 151–153, 1975.
de Klein, W. J., Recl. Trav. Chim., 96, pp. 22–25, 1977.
Carruthers, W., Some Modern Methods of Organic Synthesis 2nd Ed., Cambridge University Press, Cambridge, 1978, p. 96.

Primary Examiner—Vivian Garner
Attorney, Agent, or Firm—Linda L. Lewis; James W. Williams, Jr.

[57] ABSTRACT

Butadiene and acetic acid are reacted with metal ion oxidant to prepare acetoxyhexenoic acids which are then converted to sorbic acid.

19 Claims, 1 Drawing Sheet

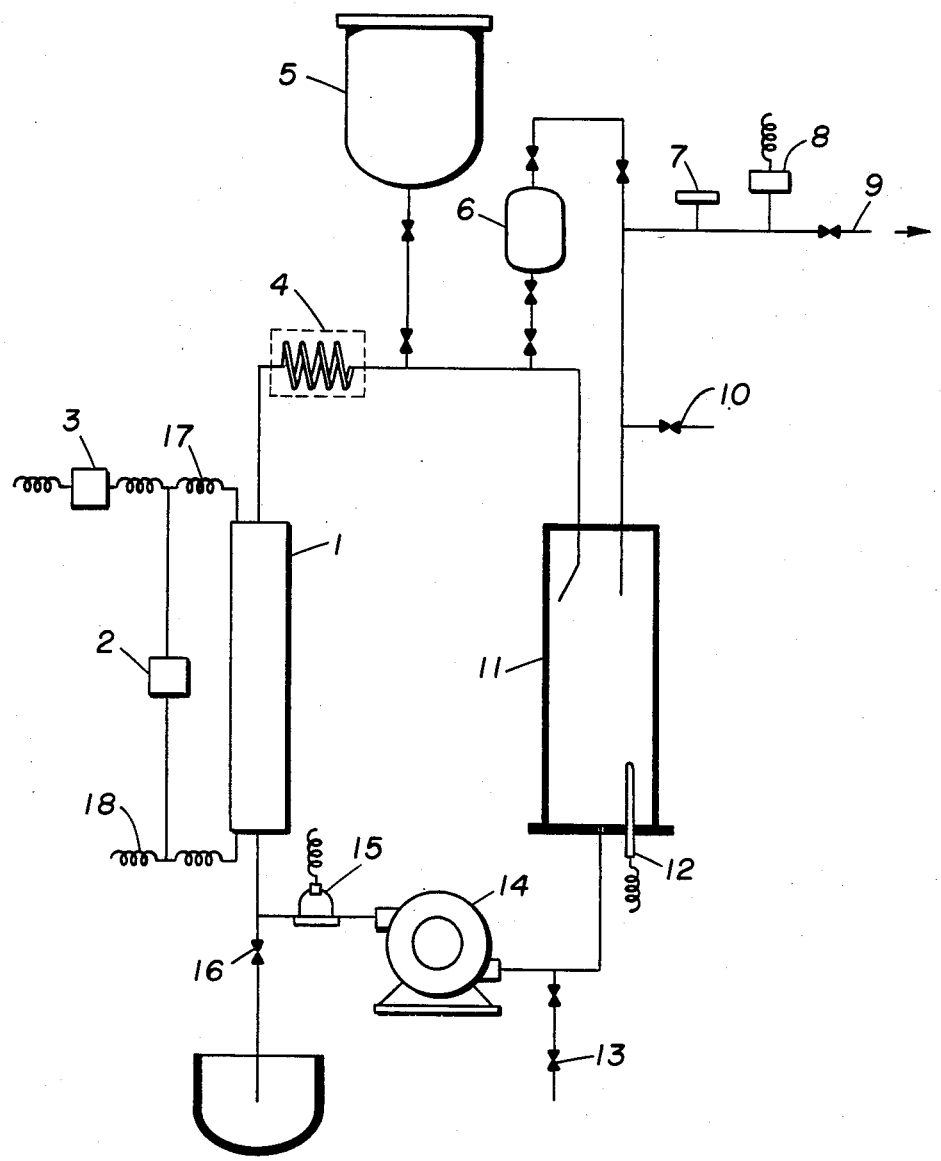

SORBIC ACID PROCESS

The present invention concerns a method of producing sorbic acid from butadiene and acetic acid in which the reactants are reacted with a metal ion oxidant to produce acetoxyhexenoic acids and the acetoxyhexenoic acids are then de-acetylated to form sorbic acid.

BACKGROUND OF THE INVENTION

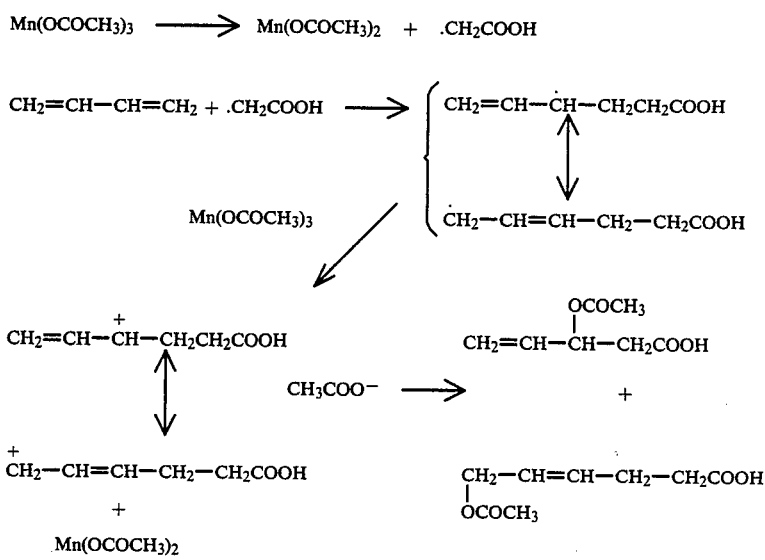

Various olefins are known to react at elevated temperatures with carbonyl compounds, e.g. carboxylic acids, in the presence of manganic compounds to produce various carbonyl compounds; for example, γ-vinyl-γ-butyrolactone is produced at 140°–180° C. by the reaction of butadiene and acetic acid. γ-vinyl-γ-butyrolactone is known to be converted to sorbic acid by heating in the presence of particular acid catalysts.

Sorbic acid is a useful article of commerce, being particularly useful in food preservation applications. Sorbic acid is presently produced commercially by a process involving reaction of ketene and crotonaldehyde.

SUMMARY OF THE INVENTION

It has now been found that butadiene and acetic acid can be reacted in the presence of a metal oxidant to obtain 6-acetoxy-4-hexenoic and 4-acetoxy-5-hexenoic acids in an efficient reaction, and that the latter acids can be separated from the metal-containing reaction mixture and readily converted to sorbic acid. The 6-acetoxy-4-hexenoic and 4-acetoxy-5-hexenoic acids are also new compounds and have useful anti-microbial, fungistatic, fungicidal and food preservative properties. In particular aspects the invention involves effecting the preparation of the acetoxyhexenoic acids with good selectivity and reaction rate utilizing manganese and copper oxidants in the reaction with electrolytic regeneration at high current density at a carbon anode, and effecting conversion to sorbic acid with good selectivity utilizing an acid catalyst, particularly an ion exchange resin.

DETAILED DISCLOSURE

The present invention in its first step involves the reaction of butadiene and acetic acid to produce the isomeric compounds, 6-acetoxy-4-hexenoic acid and 4-acetoxy-5-hexenoic acid. With manganic acetate as the metal salt, the reaction can be represented In the present invention the manganese acetate can be oxidized by electrolysis during the overall reaction and the resulting manganic acetate utilized to effect reaction of acetic acid and additional butadiene as the reaction continues. Procedures in which electrolysis is used in preparing acetoxyhexenoic acids are more fully described in out simultaneously-filed copending application Ser. No. 222,200, U.S. Pat No. 4,356,317, the disclosure of which is incorporated herein by reference. However, the preparation of acetoxyacids utilizing metal ion oxidants as described herein can be accomplished without electrolysis, and various other means of regenerating the metal ion oxidants can be employed if desired.

The present process involves the reaction of butadiene and acetic acid in the presence of a metal ion oxidant. The metal ion can be various reducible metal salts or other compounds, particularly manganese, vanadium or cerium salts in higher valent form. The metal will have a valence higher than the lowest valence above the zero valent form. In the discussion hereinbelow manganese will generally be used as illustrative of such metals, and in fact is ordinarily preferred. While the manganese can be supplied in various forms, it will preferably be in the trivalent state for the reaction.

It is important to the value of the present process that the trivalent manganese can be readily regenerated electrolytically in the presence of the other reaction components and products. For the preparation of acetoxyacids, two moles of manganese are needed for each mole of butadiene. However, the facile regeneration makes it feasible to employ only a small proportion of manganese in the reaction, e.g. about 0.1 mole per mole of butadiene, or about 5% of stoichiometric amount. It is advantageous to work with small amounts of manganese, e.g. 5% or less by weight of the reaction mixture, in order to avoid or minimize problems in handling reaction mixtures containing large amounts of poorly soluble salts. It has been found feasible to conduct the electrolysis during the reaction in the presence of various reaction components, despite the possibility of competing reactions at the anode or cathode. Among such possible reactions are reduction or polymerization of butadiene at the cathode and plating out of manganese at the cathode. It is also possible to have anodic initiated polymerizations, or to oxidize butadiene to diacetoxy compounds at the anode. However, despite the foregoing it has been found advantageous to use less than stoichiometric amounts of manganese and to electrolytically regenerate trivalent manganese during a reaction to form acetoxyhexenoic acids from butadiene and acetic acid.

With olefins other than butadiene, conditions similar to those of the present process can produce a variety of products, including unsaturated acids, saturated acids, lactones and telomers. The present reaction, involving a diolefin, presents possibilities of reactions different from those with monoolefins. It has been found that the reaction can be directed toward the 6-acetoxy-4-hexenoic and 4-acetoxy-5-hexenoic acids. This is advantageous, as it has further been found that these isomeric acids can be readily converted to sorbic acid. It is fortunate that the acetoxyhexenoic acids are produced, rather than a hexadienoic acid, as the latter could react with the metals in the reaction mixture and present a difficult separation problem and product loss.

It has been found that the presence of copper ion greatly improves the selectivity of the reaction to the desired acetoxyhexenoic acids. It is believed that the present reaction involves formation of a carboxymethyl radical from acetic acid, which then adds to butadiene forming a radical adduct; and that the latter is then oxidized to a carbonium ion. Apparently the copper ion is instrumental in accelerating the conversion to a carbonium ion, and, fortunately does not interfere by similarly oxidizing the carboxymethyl radical at an earlier stage. The oxidation of the radical adduct is helpful in directing the reaction toward the desired acetoxyacids, and avoiding telomerization, oligomerization or similar reactions of the radical adduct. The copper also appears to be effective in some way in accelerating the reaction of trivalent manganese, thereby lessening the concentration of trivalent manganese and lessening the amount of its reduction at the cathode, with consequent improvement in current efficiency. The applicants are not to be bound to a particular mechanism, as the copper ions are beneficial and effective in improving selectivity to the desired acetoxyacids and efficiency of the electrolytic process, regardless of what the mechanism may be.

Copper ions are, of course, known to be electrolitically oxidizable and reducible. The copper in bivalent form can act as an oxidant, and it is believed this is the primary mode in which copper is effective in the present process. In acting as an oxidant, the copper is reduced to monovalent copper, and this is regenerated at the anode to bivalent copper, whether directly or by reaction with trivalent manganese Thus the electrolysis is useful in effecting regeneration of the bivalent copper, as well as the trivalent manganese. However, the use of copper in the electrolysis system does present some difficulties. Copper is reduced at the cathode and has a tendency to plate out on the cathode. As the cathode becomes plated with copper, there is an increasing loss of butadiene by reduction to butene at the cathode. Various procedures can be adapted to lessen the copper deposition or otherwise minimize the butadiene reduction.

As apparent from the discussion of the present invention, a number of different reactions are occurring in the first step of the present process. Consequently, for purposes of control it is desirable to regulate certain parameters so that the various reactions will occur in desirable ratios. The electrochemical conversion of divalent manganese to trivalent manganese occurs readily, and accordingly, the size of the electrodes, or the dwell time for electrolysis in a continuous system, can be kept relatively low. Correspondingly, a reservoir can be kept in the reactor for the chemical reaction to be completed. The concentration of divalent manganese in the vicinity of the anode can advantageously be relatively high in order to minimize oxidative attack on the butadiene or acetate ion. A fairly high concentration of butadiene provides availability to react with the carboxymethyl radicals generated in the process. Fairly high concentrations of butadiene are particularly advantageous when copper salts are utilized along with the manganese salts. There is a marked improvement in selectivity to acetoxyhexenoic acids, due to the copper, under such conditions. This is important since the higher butadiene concentrations are also preferred for the improved reaction rates. In the absence of copper, high butadiene concentration may increase production of side products. Such concentrations of butadiene will generally be greater than about 0.25 mole per liter, and often greater than about 1 mole per liter, and may range up to about 5 mole or mole per liter, or possibly to solubility limits under the reaction conditions, with pressure being necessary to obtain the higher solubilities.

The acetoxy acid preparation is suitably conducted under mild temperature and pressure conditions. Atmospheric pressures can be utilized, but it may be found useful to utilize pressures slightly in excess of atmospheric to increase the solubility of butadiene in reaction media. Still higher pressures can be employed, but such are unnecessary and involve additional expense. Elevated temperatures are useful in increasing speed of the reaction, but relatively mild temperatures are generally sufficient, such as in the range of about 60° to about 120° C., or about 80° to about 160° C. Higher temperatures can be employed, but as the temperature is increased, there is a greater tendency toward production of polymers of butadiene, as well as a possible need for pressurized vessels. The acetoxyhexenoic acids are still reasonably stable at temperatures up to 140° C. and on up to 250° C. or so in the presence of acetate salts, and particularly in the presence of acetic anhydride.

The present invention involves production of an acetoxyhexenoic acid intermediate which has moieties found in butadiene and acetic acid. However, acetic anhydride is advantageously utilized in the process along with acetic acid, and it may be that either the carboxymethyl or acetoxy moieties of the product come from the acetic anhydride. Also, the acetic components may come from manganese triacetate, rather than directly from acetic acid. Even so the present reaction can be characterized as a reaction of butadiene and acetic acid, and such reaction as used herein includes all of the foregoing variations in reaction components.

The acetoxy hexenoic acids are produced in good yield in the process. The acids are formed and present in the reaction mixture along with the butadiene, acetic acid and acetic anhydride components of the mixture, and the metal components of the mixture. The acetoxyacids are separated from the reaction mixture to have a product suitable for conversion to sorbic acid. However, a complete separation is not necessary as a crude acetoxyhexenoic acid can be converted to sorbic acid. It will generally be desirable to effect a fairly complete separation from the metal components, and this is further appropriate in order to recycle the metal ions to the reaction. The acetic acid can be present during the conversion to sorbic acid. Even so it may be found convenient to separate part or all of these components as an aid to effecting separation from the metal salts, or in order to recycle the components to the reactor. It will generally be desirable to remove the butadiene component for recycle. In a laboratory procedure, butadiene and acetic acid and anhydride can be stripped off under reduced pressure with heating, and the residue partitioned between ether and water, with the acetoxyacids being found in the ether and the metal salts in the water. The ether can then be flashed off and the residue utilized for conversion to sorbic acid. In a procedure potentially suitable for large scale operations, the volatile butadiene and part of the acetic can be flashed off, and then an organic solvent added to dissolve the acetoxyhexenoic acids, and filtration under pressure can be utilized for separation from the precipitated metal salts. It is not necessary to distill the acetoxyhexenoic acids from higher boiling material prior to conversion to sorbic acids. Also, substantial amounts of acetic acid or other solvents can be present during the conversion, and in fact, it is generally desirable to have a solvent present during the conversion.

In effecting the first step of the present process, it is amost a requirement to have acetic anhydride present along with the acetic acid and butadiene reactants. The acetic anhydride has a very significant effect on the rate of the reaction, and in fact the reaction rate is generally very poor in the absence of acetic anhydride. However, it is also desirable to have substantial amounts of acetic acid present, as the acetic acid provides better salt solubility than acetic anhydride. Aside from solubility and reactivity aspects of the reaction medium, it is desirable to have conductivity sufficient to avoid unnecessarily high electrical resistance with attendant energy costs if electrolytic regeneration is used. The amounts of acetic anhydride when present can vary considerably, but will usually be in the range of about 0.1 to about 5 moles per mole of acetic acid, and preferably in the range of about 0.2 to about 0.8 moles per mole of acetic acid, although amounts up to about 1.5 moles per mole of acetic acid can be used with fairly good results. In addition to affecting the reaction rate, the acetic anhydride affects the reaction by directing it toward the acetoxyacids, rather than lactone. In the absence of the anhydride, there may be water present in the reaction mixture from the addition of hydrated manganese salts. The acetoxyacids are prone to hydrolysis in the presence of water, and the resulting hydroxyacids can cyclize to the lactone. However, if acetic anhydride is present, it serves to take up the available water, forming acetic acid. Thus the acetic anhydride serves to stabilize the acetoxyhexenoic acid products. The acetic anhydride may contribute further to the formation and stabilization of the acetoxyhexenoic acids, by means other than involved in taking up water. It appears that other means of avoiding the presence of water, or drying the reaction mixture, could be substituted for the use of acetic anhydride, and the reaction could then produce acetoxyhexenoic acids in the absence of acetic anhydride. However, the acetic anhydride has a beneficial effect on reaction rate and is also very convenient for use, and alternate procedures may compare unfavorably. Other acid anhydrides can, if desired, be substituted for acetic anhydride, although there is generally no advantage in such substitution. For example, alkanoic acid anhydrides, particularly those of lower alkanoic acids can be used, as can benzoic acid anhydrde. Such anhydrides may result in some replacement of acetoxy groups by other acyloxy groups or otherwise contribute to obtaining a mixture of products.

Solvents can be utilized in the acetoxy acid preparation to attain solubility of the reaction components in the reaction mixture. As acetic acid is a reasonably good solvent, the use of solvents other than the reaction components is ordinarily unnecessary. However, other solvents can be employed if desired. Other carboxylic acids can be employed, although such acids tend to interfere by competing with acetic acid in the reaction; suitability will depend upon relative reaction rates and the amount of side product which is acceptable. For electrolytic efficiency, it is preferred to use polar solvents or other solvents of relatively good electrical conductivity such as acetic acid.

The manganese ion utilized for effecting oxidation in the present process is primarily trivalent manganese, but the manganese can be supplied to the reaction in practically any form capable of forming manganese ions in the reaction mixture. If the manganese is supplied in divalent form, it is converted to trivalent manganese by electrolysis for reaction in the process. If provided in a higher than trivalent form, it can initially react as an oxidant in such form and subsequently be regenerated by electrolysis as trivalent manganese for further reaction in the process. The manganese can conveniently be supplied as manganic acetate dihydrate, anhydrous manganic acetate, or as a mixture of manganese dioxide and acetic acid.

Cerium has two positive valence states, 3 and 4, and can be conveniently supplied in the higher valence state as ceric acetate. It can also be supplied in any other form capable of forming ions in the reaction mixture, and oxidized to the tetravalent state if necessary by electrolysis.

Vanadium has three positive valence states, 2, 3 and 5, and can conveniently be supplied in the higher valent vanadic forms as the acetate. It can also be supplied in any other forms capable of forming ions in the reaction mixture, and oxidized to the tri- or pentavalent state by electrolysis.

The electrolysis for regeneration of higher valent metal can be conducted in an electrolysis cell comprising a container or vessel with electrodes. The desired oxidation of the metal ion occurs at the anode, and it is advantageous to utilize an anode material facilitating this oxidation. Carbon anodes have been found suitable, particularly porous carbon as such unfilled carbon electrodes give better results than pitch-impregnated graphite. High surface area carbon anodes are especially useful, as contributing to effectiveness of high current usage without significant loss in product selectivity. Various carbon fiber or particulate carbon electrodes are known to the art and can be used with advantage, such as carbon cloth and carbon felt electrodes. Some such materials have very high reported surface areas, such as 32.5 square meters per square centimeter of geometric surface, although a lesser part of such surface area would be contacted by an electrolyte. Other anode materials of high oxygen over potential are suitable in theory, but it happens that platinum tends to cause ready polymerization of butadiene, making it impractical for use unless at very low current densities, or possibly in some high surface area configuration. Moreover, the manganese containing reaction medium is highly corrosive and tends to dissolve or corrode many potential electrode materials under electrolysis conditions. Dimensionally stable metal oxide or alloy electrode materials may be suitable as anodes, as well as gold or some other noble metals. In essence the anode is one which is suitable for effecting oxidation of manganous ion in the presence of acetic acid and butadiene, which may eliminate materials with an undue propensity to effect polymerization of butadiene in such environment. The anode, as well as the cathode if it contacts the manganese containing medium, will preferably be resistant to corrosion by the medium.

High surface area electrodes will preferably have many times that surface area calculated from the planar dimensions assuming a flat, planar surface, such as 10 times such area, or advantageously 100 or more times such surface area. The actual effective surface area is uncertain, but calculations can be made assuming a penetration into a fiber or similar electrode of 0.2 mm. or so. The cathode is essentially a counter electrode in the cell to complete the electric circuit and does not effect a reaction essential to the process. Conventional electrode materials can be employed as cathode, including various carbons, metals and alloys. However, the cathode can still affect the process with regard to electrical efficiency and side reactions. The cathode reaction would preferably be limited to reduction of hydrogen ion with generation of hydrogen, but is likely to involve some reduction of metal ion or other components of the reaction mixture. For example, trivalent manganese can be reduced to divalent manganese, and copper can be reduced to the metal with plating out on the cathode. Also butadiene can be reduced to butene at the cathode. To some extent, the cathode material will affect these undesirable reductions. Carbon cathodes, particularly, graphite, have been found convenient for use. The undesirable cathode reactions can also be lessened by various techniques of cell or electrode design, or by control of relative concentrations of components. For example, a divided cell can be employed in which the electrodes are separated by a semi-permeable membrane and only particular ions are permitted to migrate across the membrane. Or the cathode can be covered by a porous membrane to lessen contact of the reaction medium with the cathode. The concentrations of various components and electrolysis current can be selected with a view to having a relatively high concentration of reducible metal components near the cathode, compared to the butadiene concentration there.

The electrolysis cell will utilize the reaction mixture as the electrolysis medium. It will be understood, of course, that in a continuous process the reaction mixture will change with time and extent of reaction, product separation, recycle of various components and introduction of additional increments of components. For large scale operations it is contemplated that the cell will have electrodes of relatively large area which are separated by a relatively short distance, and that the reaction mixture will be circulated between the electrodes. The electrolytic regeneration of the trivalent manganese will be taking place at the same time as the reaction utilizing the trivalent manganese in the production of acetoxyhexenoic acids. Both the electrolytic and chemical parts of the reaction can be conducted in an electrolysis cell between the electrodes. However, as the rates of the reaction may differ, it is preferable to have part of the reaction mixture in an electrolysis cell and part of it in an additional chamber or portion of the same chamber. The chambers can then be sized and the circulation rate between the electrodes regulated so as to obtain suitable sojurn times without unnecessarily large electrode areas. The trivalent manganese will be regenerated to an extent suitable for the chemical reaction, being recirculated between the electrodes at a rate suitable for this purpose, and the reaction mixture will be held in the reaction chambers for time sufficient to obtain the desired degree of conversion to acetoxyhexenoic acids. The process is capable of achieving high conversions, such as better than 95% based on butadiene. Since acetic acid is often used in large excess, the conversions on acetic will generally be lower. Since butadiene can be recycled, it may at times be preferred to have less than maxium conversion in a continuous process, balancing needs for suitability of reaction rate and product selectivity with suitable conversion. In a continuous process a product stream can be taken off at a rate to permit the desired conversion. Aside from recycle of reactants and electrolyte after separation from product, a stream or portion of the reaction mixture will be continuously circulating between the electrodes of the electrolysis cell.

In addition to metal salt oxidants, it is desirable to have other salts present in the reaction mixture to improve conductivity. Alkali metal salts are among those suitable, and it is convenient to utilize alkali metal acetates, e.g. sodium or potassium acetates, in order to avoid the unnecessary presence of anions other than acetate. Moreover, the alkali metal acetates, particularly potassium acetate, appear to contribute to selectivity to and stability of the desired acetoxyhexenoic acid products. Various other electrolyte salts can be used if desired.

In large scale electrolytic operation there is advantage in having electrodes separated by only a narrow gap, with electrolysis medium flowing between the electrodes, and a reservoir to hold the balance of the electrolysis medium. A convenient flow electrolysis system is illustrated in the FIGURE. The electrolysis cell 1 has electric leads 17 and 18 across which voltmeter 2 is connected and with ammeter 3 in lead 17. The exit line from the top of the cell has an optional heat exchanger 4, and inlets for solvent electrolyte charge from vessel 5 and butadiene from cylinder 6 and leads into reservoir 11. Rupture disc 7, strain gauge 8, vent 9 and gas sample valve 10 are also provided. The reservoir has themocouple 12 for temperature measurement. The exit line from the reservoir has a valve for liquid sampling at 13 and leads to pump 14 for cycling through orifice -D.P. Cell 15 for flow measurement and into cell 1, and is also provided with a drain valve for draining at 16. The electrolysis cell 1 contains two parallel carbon electrodes (not illustrated) separated by a one-eighth inch polytetrafluoroethylene gasket, with entry and exit plenums (not illustrated) so that the electrolysis medium can flow between the electrodes. The various procedures described herein for producing acetoxyhexenoic acids can, if desired, be adapted to use in the illustrated flow electrolysis system. Further description of procedures for carrying out the first step of the present process, particularly involving electrolysis, is found in our aforementioned patent application.

The following examples are illustrative of the invention.

EXAMPLE 1

A 600 ml. glass-lined pressure reactor equipped with a dip tube, thermocouple and pressure gauge, was modified to contain electrodes. The area of the graphite electrodes exposed to the reaction medium was 31.6 cm$^2$ and the electrode separation was 3.1 cm. A porous polytetrafluoroethylene membrane covered the cathode. The cell was charged with acetic acid, 110 ml., acetic anhydride 110 ml., sodium acetate, 25 grams, manganous acetate tetrahydrate, 12.5 grams, and 27 grams butadiene. Electrolysis and reaction was carried out at 0.5 ampere for 9.4 hours while the temperature was maintained at 95°-97° C. The pressure increased from 56 to 76 psig, and the applied voltage (to maintain constant current) increased from 18.5 to 23.5. The reaction mixture was stirred for continuously pumping head gas through a sparge tube between the electrodes. At the end of the alloted reaction time, the reaction mixture was heated to evaporate volatiles and the residue was partitioned with diethyl ether and water to effect separation of organic products and salts. The ether was evaporated from the ether layer, leaving crude acetoxyhexenoic acids. Determination of acetoxyacids was accomplished by vapor phase chromatographic analysis of a silylated sample of the crude product, using ethyl myristate as standard. Analysis showed 3.4 grams of acetoxyacids for a current efficiency of 22.5% to this product. The acetoxyacids were identified as 6-acetoxy-4-hexenoic acid and 4-acetoxy-5-hexenoic acid by comparison with an analysis of previously identified samples of these acids, obtained in a similar procedure.

A dip tube sample of the reaction mixture had been taken at the end of the reaction time, and this was analyzed for butenes by vapor phase chromatography, using hexane as an internal standard. The amount of butene was 0.74 gram, for a current efficiency of 15%.

EXAMPLE 2

The cell of Example 1 was charged with 147 ml acetic acid, 73 ml acetic anhydride, 25 grams sodium acetate, 12.5 grams manganeous acetate tetrahydrate, 3.7 grams cupric acetate monohydrate, and 28.4 grams butadiene. The cathode was covered by a porous polytetrafluoroethylene membrane. Reaction with electrolysis was carried out at 1 ampere current for 6.25 hours, with a decrease in voltage from 35 to 32 volts, and increase in pressure from 74 to 126 psig. Product separation and analyses were carried out as in Example 1, showing 17.3 grams of acetoxyhexenoic acids, for a 73% current efficiency, and 5.7 grams butenes, for an 83% current efficiency.

EXAMPLE 3

A reaction was carried out utilizing reaction mixture components as in Example 2, but without a membrane on the cathode. A 0.5 ampere current was maintained for 21.4 hours as voltage fell from 14 to 12 volts and pressure increased from 80 to 86 psig. Analysis showed 11.4 grams of acetoxyhexenoic acids.

EXAMPLE 4

Heating in the presence of an acidic catalyst was employed to convert acetoxyhexenoic acids to sorbic acid. An 0.8 gram amount of a mixture of 4-acetoxy-5-hexenoic acid and 6-acetoxy-4-hexenoic acid in 5 ml. 1,4-dioxane was heated to reflux in the presence of 1.5 gram of an acidic ion exchange resin, Amberlyst ® 15, for 5 hours. The yield of sorbic acid was 85%. The yield is believed to include a small amount of stereo isomers of sorbic acid, as is the case with other sorbic acid results reported herein.

EXAMPLE 5

A 0.8 gram amount of the crude mixture of acetoxyhexenoic acids from Example 3 in 5 ml. glacial acetic acid was heated at reflux in the presence of the Amberlyst ® acidic resin for 1.5 hours to give a 79% yield of sorbic acid and its isomers.

EXAMPLE 6

A divided electrochemical cell was utilized for an acetoxyacid preparation. The plate-and-frame divided electrochemical cell was constructed of stainless-steel back-plates with Teflon ® gaskets used to form the anolyte and catholyte passages. Anode and cathode surfaces were 6 cm × 15 cm with inlets at each end of the longer dimension. Inlet and exit were tapered at about 45° to aid streamlined flow. The anolyte and catholyte compartments were separated by a membrane of Nafion ® 425 sulfonated polyether polymer. Spacers provided ⅛' of gap between the membrane and each electrode such that the overall cell gap was ¼". Within each compartment was a mesh of polyethylene with approximately ~¼" square grids and having a thickness of ~⅛ (CONWED XN-5050). The mesh rested against the electrodes, masking each such that the effective area of each electrode was about 40 cm². Each cell compartment was connected by pumps and piping to its own steam heated reservoir. Gaseous 1,3-butadiene was sparged into the anolyte continuously, maintaining a saturated solution of the diene.

In the cell, an anode of Union Carbide WDF graphite felt (~¼" thick) and a cathode of stainless steel were used. An anolyte solution consisting of
  $Mn(OAc)_2.4H_2O$: 50 g. (200 mmol)
  KOAc: 150 g. (1.53 mol)
  $Cu(OAc)_2.H_2O$: 14.6 g. (73 mmol)
  HOAc: 590 ml
  $Ac_2O$: 290 ml
and a catholyte consisting of
  KOAc: 120 g. (1.22 mol)
  HOAc: 880 ml
  $Ac_2O$: 35 ml
were charged into their respective reservoirs. (Ac indicates the acetyl radical, and OAc the acetate anion). The solutions were maintained at ~105° C. and circulated through the cell (anolyte flow rate ~1.2 l/min., for a linear rate of ~21 cm/second; catholyte flow rate ~0.5 l/min.).

The system was electrolyzed at a constant current of 5 amps (125 mm/cm²) (~12 volts) for three hours. After this time a sample of anolyte was taken, treated with $H_2O$, and silylated with Regisil ® (Regis Chemical). VPC analysis showed a total of 45.7 g of a mixture of 4-acetoxy-5-hexenoic acid and 6-acetoxy-4-hexenoic acid corresponding to a current efficiency of 95%.

55 g. (561 mmol) of KOAc was added to the catholyte and the system was electrolyzed for 3 hours at 5 amps. An anolyte analyzed by VPC as above showed 80.5 g of the mixture of acetoxy acids corresponding to an overall current efficiency of 84%. The anolyte was distilled under reduced pressure to remove most of the acetic acid and acetic anhydride. 200 ml of water was added and the mixture was again distilled to remove most of the liquids. The residue was dissolved in a minimal amount of water and extracted 3× with diethylether. The dried ether solution was distilled under reduced pressure to give 106 g of residue, shown by VPC to contain 79.8 g of a mixture of the acetoxy hexenoic acids. This corresponds to a current efficiency of 83%.

A divided electrolysis cell is convenient for use for the electrolytic regeneration of trivalent manganese and substantially avoids the problem of butadiene or trivalent manganese reduction at the cathode. Semipermeable membranes can be employed as divider which permit transmission of ions to carry current, e.g. hydrogen or alkali metal ions, or such ions in hydrated form, but substantially prevent transmission of other ions or molecules. Membranes of cation exchange resins are particularly suitable, e.g. those containing sulfonic groups, but anion exchange resins can also be used. The Nafion ® fluoropolymer resin membranes have been found useful, such membranes being composed of fluorinated hydrocarbon resin with pendant ether groups having sulfonic acid substituents. The reaction medium employed in the process is circulated through the anode chamber as anolyte. The catholyte can be electrolyte medium capable of carrying current, but it will generally be desirable to use some components common to the anolyte, such as acetic acid, potassium acetate, acetic anhydride, etc. in order to avoid contamination or dilution of the anolyte by leakage from the catholyte.

Some chemical procedures for preparation of acetoxyhexenoic acids with manganic acetate, with and without co-oxidant were carried out in accord with the following general procedure.

To a 6 oz. Fisher-Porter bottle is added 20 mmole $Mn(OAc)_3 2H_2O$, 10 mmole of desired co-oxidant and 150 ml of 2:1 $AcOH:Ac_2O$. To this is added 110 mmoles or other designated amount of butadiene. A Teflon-coated magnetic stirring bar is added and the bottle sealed. The apparatus is lowered into a constant temperature oil bath heated to 95°–97° C. and the reaction is allowed to continue until the characteristic Mn(III) color is gone. The reaction is allowed to cool to room temperature. The solvent is removed on a rotary evaporator in vacuo at 45° C. until solids remain. $H_2O$ is added and the solids are dissolved. After stirring for several minutes the pH is adjusted to 2 with conc. HCl (pH followed via pH meter). The aqueous layer is then extracted 3 times with diethyl ether. The pH of the aqueous layer is re-examined and if necessary re-adjusted to pH of 2 and re-extracted. The combined ether extracts are dried with anhydrous $MgSO_4$ and the ether is removed in vacuo. A portion of the remaining product is silylated and analyzed via gas chromatography using a Varian 3700 fitted with a 3 mm×2-meter ov-101/Chromosorb W column. Conditions: 80° to 240° C. at 8°/min, He carrier gas, Tc detector. Ethyl myristate is added as an internal standard. Integration is carried out on an Autolab System IV computer.

The results of procedures using various co-oxidants are shown in the following table.

TABLE III

| Metal Salt (mmoles) | Mn(OAc)₃ (mmoles) | C₄H₆ (mmoles) | % Yield (a) |
|---|---|---|---|
| Cu(OAc)₂ (10) | 20 | 110 | 85 |
| Co(OAc)₂ (5) | 20 | 19 | 57 |
| Co(OAc)₂ (10) | 20 | 63 | 47 |
| Co(OAc)₂ (20) | 20 | 63 | 44 |
| Sn(OAc)₂ (10) | 20 | 72 | 27 |
| Ni(OAc)₂ (10) | 20 | 65 | 12 |
| Fe(OAc)₂ (10) | 20 | 107 | 15 |
| Zn(OAc)₂ (10) | 20 | 112 | 23 |
| Cr(OAc)₃ (10) | 20 | 74 | 11 |
| Ru(acac) (0.22) | 20 | 77 | 17 |
| AgOAc (0.6) | 20 | 70 | 26 |
| Pd(OAc)₂ (0.5) | 20 | Butene diacetates and many high boilers - Pd | |

(a) Based on Mn(III)

Selectivity was much better with the cupric salt than with any of the other salts tested.

When procedures like the above were carried out without a co-oxidant, it was found that the results were affected by the ratio of butadiene to trivalent manganese, with fairly good results possible by controlling such ratio as illustrated in Table IV.

TABLE IV

| Mn(OAc)₃ (mmoles) | C₄H₆ (mmoles) | Yield of AA % |
|---|---|---|
| 20 | 58 | 27 |
| 20 | 27 | 65 |
| 20 | 12 | 46 |

In Table V, use of a low concentration of cupric salt is illustrated.

TABLE V

| Mn(OAc)₃ (mmoles) | Cu(OAc)₂ (mmoles) | C₄H₆ (mmoles) | Yield of AA % |
|---|---|---|---|
| 20 | 10 | 110 | 83 |
| 20 | 10 | (a) | 79 |
| 20 | 0.01 | 82 | 76 |

(a) C₄H₆ continuously bubbled thru at atm. pressure. Otherwise the same conditions apply.

EXAMPLE 7

A reaction was carried out in a Fisher-Porter bottle as previously described, with 75 ml acetic acid, 25 ml acetic anhydride, 5 grams potassium acetate, 40 millimoles manganic triacetate, 93 millimoles butadiene, and 1 millimole cupric acetate, with heating at 175° C. The reaction was over in 5 minutes and gave an 81% yield of acetoxy hexenoic acids and about a 1.3% yield of γ-vinyl-γ-butyrolactone. Similar resuls were obtained at higher temperatures from 154° to 210° C., but with somewhat higher yields of lactone in some cases. When a similar reaction was carried out, but omitting the acetic anhydride, the lactone was the primary product.

EXAMPLE 8

3.64 gm V₂O₅ (2×10⁻² mole) and 1.0 gm Cu(OAc)₂ (5×10⁻³ mole) were added to 150 ml of 2:1 (V/V) AcOH:Ac₂O in a 6 oz Fisher-Porter bottle (magnetic stirrer). To this was added 3.3 gm of butadiene (6.1×10⁻² mole). Reaction was allowed for 24 hrs. at 97° C. The reaction mixture was worked up and analyzed in accord with the general procedure previously described. A 35% yield was obtained based on V(V) present. It is expected that vanadium can be regenerated and utilized in the various procedures described herein illustrating re-generation and re-use of trivalent manganese.

EXAMPLE 9

A cerium (IV) ion was utilized as metal oxidant to produce acetoxyhexenoic acids in a procedure in which the cerium (IV) was electrolytically re-generated. The electrolysis cell was a glass column containing a cylindrical graphite cloth anode with a copper rod cathode in it. Reaction mixture was pumped from a reaction flask through a feed line and up through the column, and then returned to the reaction flask which was kept at 105° C. The anode had a 150 cm² geometric area, compared to only a 3.2 mm diameter cathode. The approximately 1 liter of reaction mixture was a 2:1 ratio of acetic acid to acetic anhydride with 150 grams potassium acetate and 50 grams Ce(OAc)₃. Butadiene was continuously bubbled through the reaction flask to saturate the reaction mixture with butadiene. With a 10 liter per minute flow rate through the electrolysis cell, a 5 ampere current was passed for 2 hours. Isolation of product gave 14.4 grams acetoxyhexenoic acids, for a current selectivity to this product of 45%. Some copper was present in the reaction mixture during the reaction because of the copper cathode.

Acyloxyhexenoic acids have been found to be readily converted to sorbic acid. Dehydration or deacetylation conditions are generally employed, such as heat and catalysts which facilitate dehydration and saponification reactions, e.g. acid catalysts. Various acid catalysts known to the art can be used, including both solid and liquid acidic materials. However, the acid should be a fairly strong acid, such as mineral acids and the like or strongly acidic ion exchange resins. Various metal oxides, particularly acidic metal oxides, can be employed, e.g. silica aluminas, thorium oxide, etc., and various other metal oxides known as acidic or dehydration catalysts.

While various catalysts can be used to produce sorbic acid it will be understood that some are much more effective than others. Thus some cation exchange resins give very high conversions and selectivity to sorbic acid. It happens that some of the other classes of catalysts exhibit a strong tendency to convert the acetoxyacids to γ-vinyl-γ-butyrolactone and give poor selectivity to sorbic acid. It is likely in such cases that longer reaction times or higher reaction temperatures will produce better selectivity to sorbic acid. This seems particularly the case since the lactone is known to be converted to sorbic acid in the presence of specified acid catalysts, as indicated in U.S. Pat. Nos. 4,022,822 and 4,158,741. However it is considered preferable to utilize catalysts which will convert the acetoxyhexenoic acids to sorbic acids with little side product under relatively mild conditions and in a reasonable reaction time. Even so, the catalysts in general disclosed in pages 4,022,822 and 4,158,741 can be utilized with some degree of success in the present conversion of acetoxyhexenoic acids to sorbic acid. Various catalysts which can be used herein include the ion exchange resins, Amberlyst 15, Amberlyst XN 1005, Amberlyst XN 1010, Amberlite IR-120B, all strongly acidic cation exchange resins, particularly polystyrenes with acidic groups, e.g. sulfonate groups ($-SO_3H$), and by Rohm and Haas Company under the foregoing trademarks; Nafion® N-501, a sulfonated polyfluoroether polymer; and Dowex® 50WX8 polymer, a styrene-divinylbenzene copolymer with acidic groups. Also such mineral acids as hydrochloric, phosphoric and sulfonic acids. It will be recognized that the various other catalysts can be used to supply the hydrogen ion for catalysis of the reaction. Good conversions and selectivities are obtained with some ion exchange resins. In addition the ion exchange resins have the advantage of not disolving in the acetoxyacids or their solvent, and present the possibility of more convenient separation from the sorbic acid product.

The Amberlite® and Amberlyst® ion exchange resins are further described as composed of long chains of polystyrene locked together by means of divinylbenzene crosslinks into a three dimensional, insoluble matrix. The acidic resins have sulfonic acid groups bonded to the matrix. The Amberlyst 15® resin is macroporous, and referred to as macroreticular. Amberlyst 15® is described as having a weight capacity as dry resin of 4.40 milliequivalent/gram and a calculated weight capacity as internal surface of 0.193 milliequivalent/gram; and internal surface area, 55 square meters/gram, porosity of 36% and average pore diameter of 265 angstroms.

The acetoxyhexenoic acids, particularly the 6-acetoxy-4-hexenoic and 4-acetoxy-5-hexenoic acids, in combination with strong acid catalysts constitute novel compositions, and such compositions can include one or more of any of the above described catalysts, and may also include a solvent for the acetoxyacids. Such compositions including acidic ion exchange resins are particularly useful for producing sorbic acid. The amounts of the acid catalyst and acetoxyacids can vary widely, using for example less than 1 up to more than 10 parts by weight acid catalyst per part by weight acetoxyacids, but as the catalyst, particularly ion exchange resins, can be used repeatedly, it may be advantageous to use more than an equal weight of acid catalyst.

The conversion to sorbic acid is generally carried out at elevated temperature, such as temperatures from about 60° C. up to as high as 250° C. or so, but temperatures in the range of about 80° to about 125° or possibly to about 140° C. or 160° C. may prove most convenient for use.

As disclosed herein, the acetoxyhexenoic acids can be converted to γ-vinyl-γ-butyrolactone, which is itself a useful compound for various purposes, as well as an intermediate for production of sorbic acid. It happens that one of the primary objects of the present invention is to provide a route to sorbic acid, and in this sense the lactone is a side product in the conversion of acetoxyhexenoic acids to sorbic acids. However it is still a useful development to be able to readily convert the acetoxyhexenoic acids to the γ-vinyl-γ-butyrolactone in the presence of acid catalyst as disclosed herein. In some instances the lactone may be sought as an end product, or, for some reason, it may be convenient to prepare the compound enroute to the sorbic acid.

Methods for converting acetoxyhexenoic acids to lactone are more fully described in our simultaneously filed copending application Ser. No. 222,199, U.S. Pat. No. 4,380,650. In the present process conditions are generally intended to effect conversion of the acetoxyhexenoic acids predominantly to sorbic acid, generally with selectivities to this product much greater than 50%, such as often over 70° or 80%, with very little production of lactone as final product. As described herein, good selectivity to such product is obtainable. However, the trans, trans product is generally accompanied by small amounts of its isomers, up to 5% or so, which are believed to be stereo isomers, trans-cis, cis-trans, and cis-cis. There is also a possibility that some fraction of such isomers includes position isomers in which the double bonds are in positions other than 2,4.

The acetoxyhexenoic acids can be treated with acids, such as cation exchange resins, in bulk, but the use of solvents may be convenient and often improves selectivity to the desired sorbic acid product. Acetic acid can be used as solvent and is convenient for use if the acetoxyhexenoic acids as prepared are in admixture with such solvent. Various organic solvents for the acetoxyacids can be used, including various hydrocarbon, etc. solvents, so long as the solvent does not unduly react and give undesired products. Alkanoic acids in general can be used. Dioxane gives good results, but use for preparation of food additive products may not be appropriate. Chlorobenzene gives good results, and tends to permit use of lower reaction temperatures than some other solvents. Various concentrations of the acetoxyacids can be used, but there is generally some improvement in selectivity with use of low concentrations, e.g. selectivity at 2% concentration may be 10% or so better than selectivity at concentrations of 20% or so. However, concentrations from less than 1% up to 20% or to solubility limits can suitably be used.

Acyloxyhexenoic acids are in general suitable for conversion to sorbic acid. However, such acids with acetoxy as the acyloxy group are most conveniently prepared in the first step of the present process. Acyloxyhexenoic acids where the acyloxy is the residue of other alkanoic acids, e.g. $RCH_2COO-$, where R is an alkyl of 1 to 4 carbons, can be converted to sorbic acid by procedures described herein. However, the reactions of butadiene with propionic or higher acids in the procedures described herein will result in acyloxyhexenoic acids in which there is an alkyl substituent on the 2-carbon of the hexenoic acid, corresponding to the R group of the alkanoic acid. Thus further treatment in accordance with procedures herein for conversion to sorbic acid will produce a substituted sorbic acid, i.e. with an alkyl group on the 2-position. Procedures can be utilized for preparing unsubstituted acyloxyhexenoic acids, such as using mixtures of acetic and another acid in the reaction with butadiene, and separating the mixtures of products if necessary, or by some ester exchange reaction with the acetoxyhexenoic acids. In practice, it may be that there is no reason to employ any acyloxyhexenoic acids for conversion to sorbic acid except the acetoxyhexenoic acids because of their convenience in preparation. Nevertheless other acyloxyhexenoic acids are suitable for conversion as described herein. The 6-acyloxy-4-hexenoic and 4-acyloxy-5-hexenoic acids are particularly appropriate for such conversion, but various isomers are expected to be similarly useful in varying degree. Methods of isomerization are known which will change the position of the double bond and acyloxy substituent. Ordinarily the process described herein will proceed via the 6-acyloxy-4-hexenoic and 4-acyloxy-5-hexenoic acids; however, there may be concomitant production of small amounts of various isomers or derivatives of the foregoing which are similarly converted to sorbic acid by the acid treatment described herein.

With acetic anhydride present in the reaction mixture, some of the acetoxyacids, possibly a small portion, may be in the form of a mixed anhydride with acetic acid, rather than the free acids. The extent of such anhydride formation will depend on the proportion of anhydride in the reaction mixture. For the conversion to sorbic acid, it is preferable that the acetoxyacids be in the form of free acids. Various procedures can be used to convert the small amount of anhydride to the free acid, e.g. when the acetic acid is flashed off, additional acetic acid can be added and the procedure repeated. Alternatively, hydrolytic procedures can be used. The addition of acid to the reaction product mixture may be beneficial in converting salts to more insoluble form, permitting ready removal, as in converting any residue potassium acetate in the organic portion of the product mixture, after some salt separation step, to potassium sulfate to make it more insoluble. The presence of potassium acetate and similar salts would be detrimental to an ion exchange resin used for the conversion to sorbic acid.

EXAMPLE 10

A 0.8 gram amount of acetoxyhexenoic acids in 5 ml dioxane was heated to 100° C. for three hours in the presence of 1.5 grams Amberlyst ® exchange resin, to give 98% conversion with 69% selectivity to sorbic acid and 7% to $\gamma$-vinyl-$\gamma$-butyrolactone. The sorbic acid includes a small, unascertained amount of isomers. A similar procedure using diglyme as solvent and 20-hour reaction time, gave 24% selectivity to sorbic acid.

EXAMPLE 11

A 0.8 gram amount of acetoxyhexenoic acids in 5 ml acetic acid with 1.5 grams Dowex 50W-X8 ion exchange resin was heated to 120° C. for two hours to produce 98% conversion of the acetoxyhexenoic acids with 47% selectivity to sorbic acid. The resin had been conditioned by a previous run under the same conditions.

EXAMPLE 12

A 2 gram amount of acetoxyhexenoic acids in 2 ml acetic acid with 1.5 grams Amberlyst ® 15 resin was heated to 125° C. for one-half hour to give 98% conversion, with 70% selectivity to sorbic acid, and 3% to lactone. The sorbic acid may contain a small amount of isomeric hexadienoic acids. The resin employed had been previously used in similar procedures.

EXAMPLE 13

A reaction was run with 0.8 gram acetoxyhexenoic acids in 5 ml acetic acid, employing a Nafion ® N-501 resin, 1.5 grams, at 120° for 1 hour, to give 99% conversion with 75% selectivity to sorbic acids and 8% to $\gamma$-vinyl-$\gamma$-butyrolactone.

EXAMPLE 14

A 1 gram amount of acetoxyhexenoic acids in 6 ml hydrochloric acid (37%) was heated for 2 hours at 100° C. to cause 98% conversion with 17% selectivity to sorbic acid and 69% to $\gamma$-vinyl-$\gamma$-butyrolactone. The sorbic acid may include a small amount of isomeric hexadienoic acids.

EXAMPLE 15

Utilizing amounts of acetoxyacids and Amberlyst ® 15 resin as in previous examples, the components were heated in chlorobenzene solvent at 85° C. for 2.5 hours to give 53% selectivity to sorbic acid and 7% to its isomers, with 12% selectivity to lactone. When a small amount of tetrabutylammonium iodide was also present, the selectivity to sorbic acid was 45%. Cutting the reaction time to 1.5 hours gave 47% selectivity to sorbic acid and 26% to lactone. An additional procedure in which 1.6 grams of the acetoxyacids were heated to 85° C. with 3 grams of the resin in 10 ml of chlorobenzene gave 64% selectivity to sorbic acid and 77% to sorbic plus isomers.

EXAMPLE 16

Acetoxyacids (6 g) were heated at reflux in acetic acid (11.8 g) over Amberylst 15 (3 g) resin for 0.5 hr. At the end of this time vapor phase chromatographic analysis showed a selectivity to sorbic acid isomers of 75% with a 79% mass balance.

EXAMPLE 17

The experiment described in Example 16 was repeated except that the acetoxyacids were added over a 2.5 hr. period. The selectivity to sorbic was 82% with a 89% mass balance.

EXAMPLE 18

A mixture of sorbics 2.8 g (36%, t,t, 64% other isomers) was heated at reflux in acetic acid (19 g) with Amberlyst 15 resin (3 g) for four hours. At the end of this time vpc showed 71% t,t and 21% other isomers with a 95% mass balance.

EXAMPLE 19

A mixture of acetoxyacid (1.6 g) and Amberlyst ® resin (3 g) in chlorobenzene (10 ml) was heated at 85° for 2.5 hours. The yield of sorbic acids was 72% with a material balance of 79%.

EXAMPLE 20

An experiment identical to that described in Example 19 was carried out except that sorbic acid (1 g) was charged initially along with the acetoxyacids. The yield of sorbics and mass balance decreased to 51 and 67% respectively. The yield was based on acetoxyacids, counting 1 gram of the sorbic acid product as from the original addition.

EXAMPLE 21

Several experiments are carried out using the same resin. In each run the acetoxyacid is added dropwise to the hot reaction mixture. The t,t-sorbic continuously collects in a cold crystallizer as the reaction mixture is circulated from the reactor to the crystallizer and back. At the end of a given run the crystalline sorbic is removed and analyzed. The yield in a given run is based on the amount of t,t found in the crystallizer vs the amount of acetoxyacids added. The recycle stream is analyzed and reused in the next batch run. In a given set of experiments the reactions are carried out so that the recycle stream contains the same concentration at the beginning of each run. The flow rate is approximately 15 ml/min. The crystallizer is kept at 5°–10° C.

The reactor was charged with 161 g of a mixture of acetic acid and nonane (¼, v/v) and Amberylst 15 resin (25 g). When the temperature in the reactor reached 117°, addition of the acetoxyacids (39 g) was started. After three hours the addition was complete and after 4.5 hours heating was stopped. A 30% yield of t,t sorbic was obtained. Three additional experiments were carried out and the yields of sorbic acid were 64, 72 and 70% respectively.

What is claimed is:

1. A process for preparing sorbic acid which comprises reacting butadiene and acetic acid in the presence of acetic anhydride and one or more metal ion oxidants selected from manganese, vanadium and cerium ions at temperatures of about 60° to about 250° C. under conditions to produce acetoxyhexenoic acids, comprising 6-acetoxy-4-hexenoic acid and 4-acetoxy-5-hexenoic acid, effecting a separation so that the acetoxyhexenoic acids are substantially free from metal ion component, and converting the acetoxyhexenoic acids to sorbic acid by contact with an acid catalyst at temperatures of about 60° to about 250° C.

2. The process of claim 1 in which an acidic ion exchange resin is used as catalyst to convert the acetoxyhexenoic acids to sorbic acid.

3. The process of claim 1 in which the butadiene and acetic acid are reacted in the presence of and alkali metal acetate.

4. The process of claim 1 in which the butadiene and acetic acid are reacted at temperatures of about 80° C. to about 160° C.

5. The process of claim 1 in which manganese is utilized as metal ion oxidant.

6. The process of claim 5 in which copper is present with manganese.

7. The process of claim 6 in which the manganese and copper repeatedly go through an oxidation reduction cycle with electrolysis being used for the oxidation of the manganese and copper.

8. The process of claim 7 in which the electrolysis is conducted with a carbon anode and continuous addition of reactants utilizing current densities at the anode in excess of 100 milliamperes per square centimeter (geometric surface) with a reaction at a rate to provide more than 0.1 gram mole acetoxyhexenoic acids per liter-hour.

9. The process of claim 8 in which a carbon fiber anode is used in the electrolysis.

10. The process of claim 1 in which separation of metal salt ion component from the reaction mixture is effected and conversion to sorbic acid is carried out in the presence of at least part of excess acetic acid which was present during the reaction with butadiene.

11. The process of claim 10 in which substantial amounts of butadiene and acetic acid are removed prior to separation of metal salt oxidant.

12. The process of converting acetoxyhexenoic acids, comprising 6-acetoxy-4-hexenoic acid and 4-acetoxy-5-hexenoic acid to sorbic acid which comprises contacting such acids with a strong acid catalyst at temperatures of about 60° to about 250° C.

13. The process of claim 12 in which the acid catalyst is an acidic ion exchange resin.

14. The process of claim 13 in which the acid catalyst is a mineral acid.

15. The process of claim 12 in which the acid catalyst is hydrochloric acid.

16. The process of claim 13 in which acetic acid is present as a solvent.

17. The process of claim 12 in which the acetoxyhexenoic acids are in solution in a solvent in a concentration in the range of about 1 to about 20% by weight.

18. The process of claim 12 in which temperature during the reaction is in the range of about 80° to about 125°.

19. The process of claim 1 in which the reaction mixture is dry and the acetoxyhexenoic acids comprise 4-acetoxy-5-hexenoic acid and 6-acetoxy-4-hexenoic acid.

* * * * *